(12) United States Patent  (10) Patent No.: US 7,300,284 B2
Linder  (45) Date of Patent: Nov. 27, 2007

(54) DENTAL IMPLANT SYSTEM

(75) Inventor: Andreas Linder, Basel (CH)

(73) Assignee: Straumann Holding AG, Basel (CH)

( * ) Notice: Subject to any disclaimer, the term of this patent is extended or adjusted under 35 U.S.C. 154(b) by 53 days.

(21) Appl. No.: 11/195,884

(22) Filed: Aug. 3, 2005

(65) Prior Publication Data

US 2006/0029907 A1  Feb. 9, 2006

(30) Foreign Application Priority Data

Aug. 5, 2004  (EP)  .................. 04018636

(51) Int. Cl.
*A61C 8/00* (2006.01)
(52) U.S. Cl. ............... 433/173; 433/172; 433/174; 433/177; 433/182
(58) Field of Classification Search ............... 433/173, 433/172, 174, 177, 182
See application file for complete search history.

(56) References Cited

U.S. PATENT DOCUMENTS

| | | | | |
|---|---|---|---|---|
| 5,108,288 A | * | 4/1992 | Perry | 433/173 |
| 5,538,428 A | * | 7/1996 | Staubli | 433/173 |
| 5,782,918 A | * | 7/1998 | Klardie et al. | 606/60 |
| 5,944,525 A | * | 8/1999 | Ura | 433/173 |
| 6,168,436 B1 | * | 1/2001 | O'Brien | 433/173 |
| 6,206,696 B1 | * | 3/2001 | Day | 433/141 |
| 6,247,933 B1 | * | 6/2001 | Wagner et al. | 433/173 |
| 6,827,575 B1 | * | 12/2004 | Jorneus | 433/174 |
| 2002/0168613 A1 | * | 11/2002 | Riley et al. | 433/173 |
| 2002/0177105 A1 | * | 11/2002 | Engman | 433/173 |
| 2003/0054318 A1 | | 3/2003 | Gervais et al. | |
| 2004/0096804 A1 | * | 5/2004 | Vogt et al. | 433/173 |
| 2004/0180308 A1 | * | 9/2004 | Ebi et al. | 433/173 |
| 2005/0266383 A1 | * | 12/2005 | Aravena et al. | 433/173 |

FOREIGN PATENT DOCUMENTS

FR  2 733 902  11/1996
WO  WO 98/40029  9/1998

* cited by examiner

*Primary Examiner*—Melba N. Bumgarner
*Assistant Examiner*—Jonathan Werner
(74) *Attorney, Agent, or Firm*—Scully, Scott, Murphy & Presser, P.C.

(57) ABSTRACT

An implant system comprising a dental implant, a holding element is provided with non-rotational joint means adapted to avoid relative rotation of the holding element with respect to the implant, and a clamping element adapted to steady retain the holding element close to said implant. The system further comprises release means provided on the clamping element and suitable to interact with release means provided on a separating tool, so that acting on the separating tool the implant can be released from the holding element without transferring damaging forces such as torsional, tensile or compressive forces, to the implant.

19 Claims, 5 Drawing Sheets

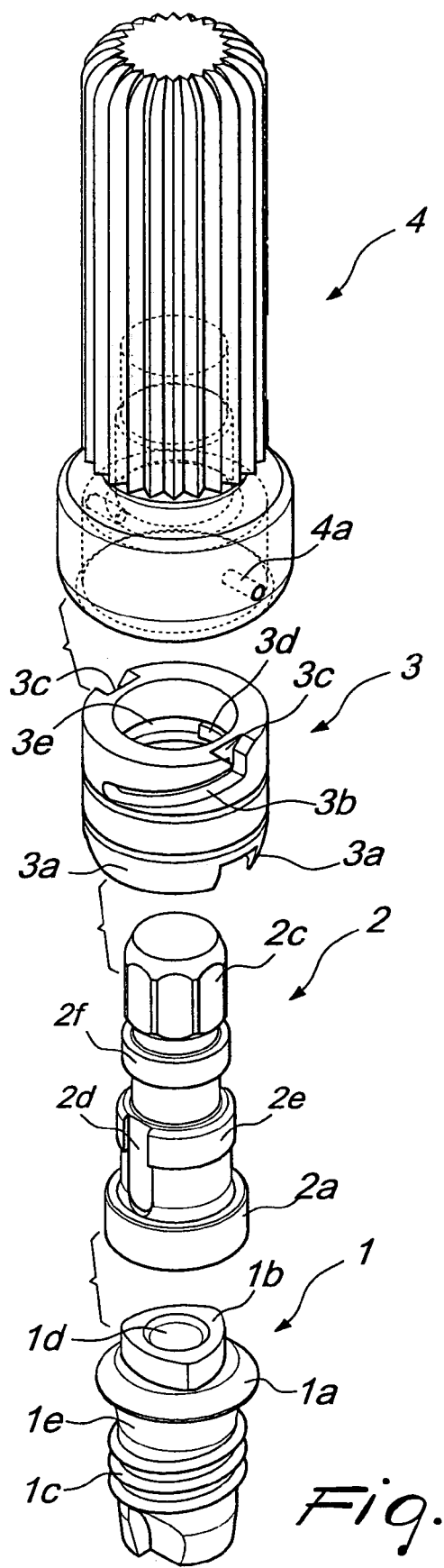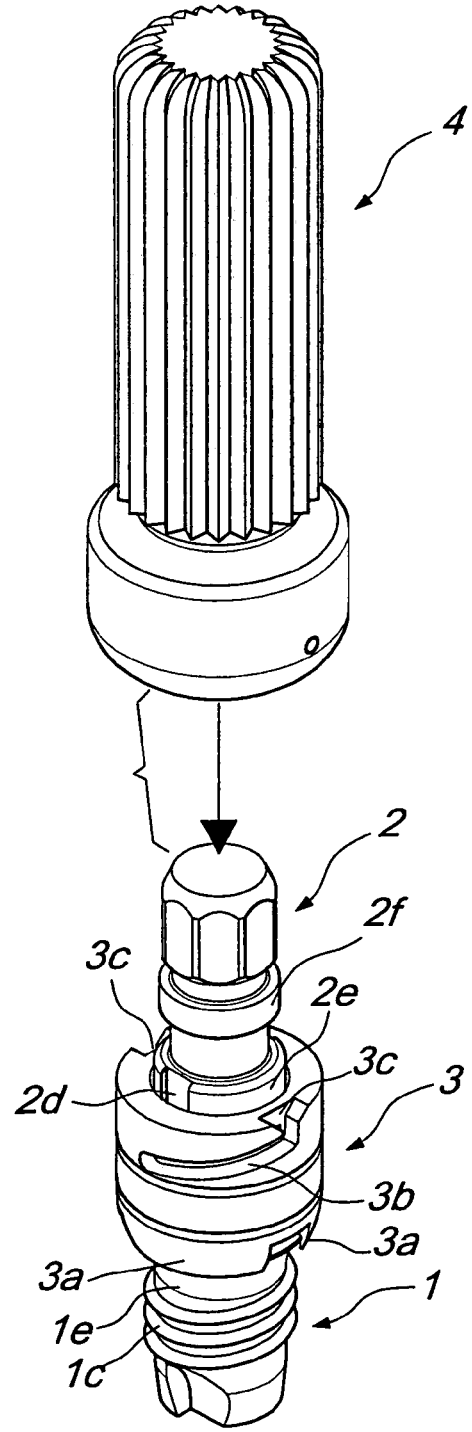

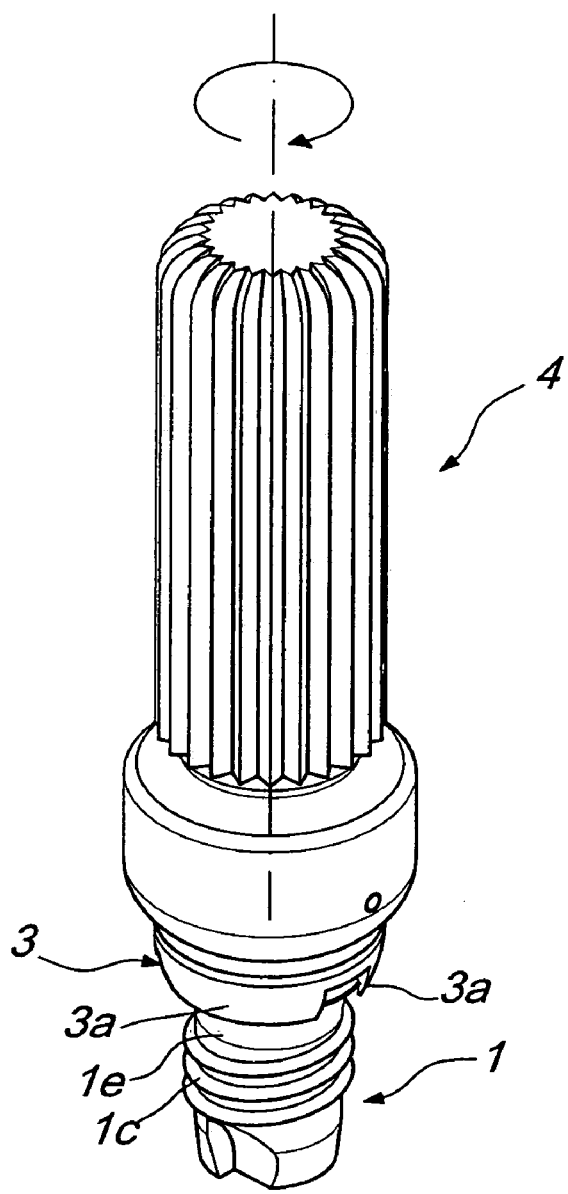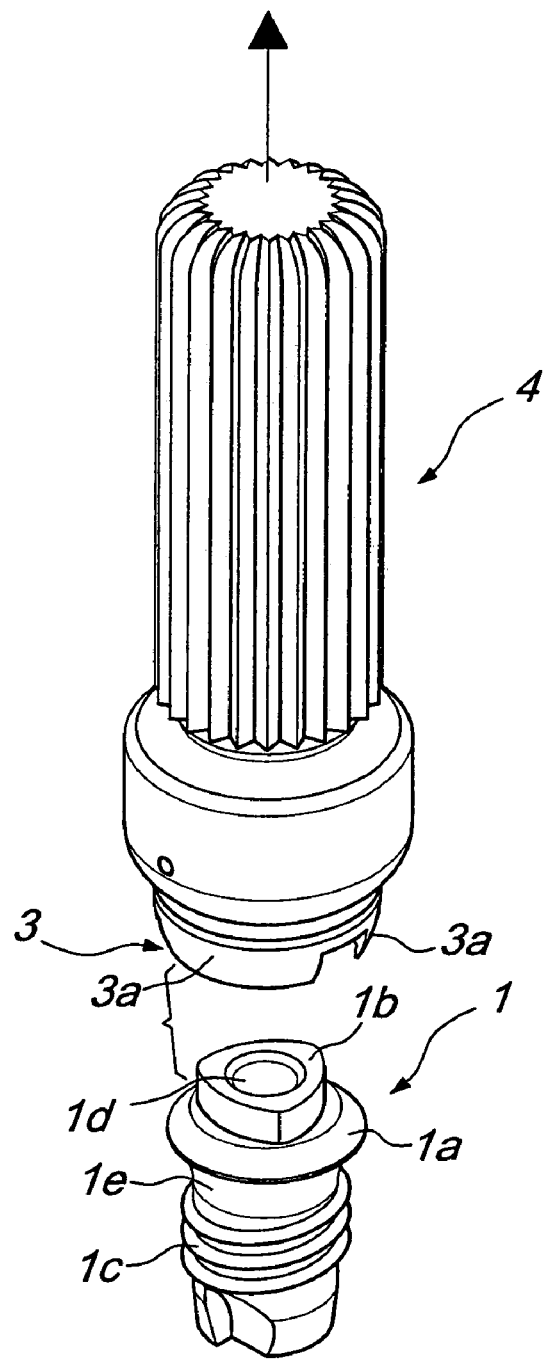
Fig. 3
Fig. 4

DENTAL IMPLANT SYSTEM

The present invention relates to an implant system, particularly a dental implant system, comprising an implant suitable to be positioned and retained in the bone tissue and means suitable to hold, to position in the bone tissue, and to release in its final seat said implant without directly taking said implant with the hands or contacting it with any contaminating agent and simultaneously minimizing the transmission of damaging forces, such as compressive, tensile and torsional forces from the tools to the implant and consequently from the implant to the bone tissue. In order to achieve this aim, the system further comprises a holding element to hold and to position said implant in its final seat, and a separating tool for removing said holding element from the implant after implantation, said holding element and said separating tools being suitable to interact in order to remove said holding element from said implant by transmitting minimized damaging forces to the implant.

BACKGROUND OF THE INVENTION

Generally, implants are used in dental surgery or in bone surgery to reconstruct teeth or bone parts of a human being. Usually, implants are intended to be inserted by screwing or pressing into a receiving bore which has been prepared e.g. in the bone tissue. The preparation consists of a conventional surgical procedure. For applications in the dental sector, usually an incision is made along the gingival tissue at the position where the implant is going to be inserted. Successively, a cylindrical bore is drilled into the bone tissue in order to insert the implant therein.

Implants are mostly provided with a holding element, which usually is fixedly secured to them by a screw or through screwing, and in this case the holding element is provided with an external screw thread.

A holding element for implants can be employed during a number of different production phases of implants, while preparing them for a surgical intervention, and directly during implantation. One primary application of the holding element is to provide the option of attaching a handhold in order not to touch the implants directly and in this manner to keep them sterile. Another application of holding elements is to offer the option of attaching manipulating members thereto for further processing of the implant. This facilitates the handling of the implants even during their production.

In case of an implantation, the holding element permits to extract the implant from a sterile container, for example an ampule, and to implant it without direct contact with contaminating agents by means e.g. of a manipulating tool gripped to the holding element and through the holding element gripped to the implant itself. By operating only on the manipulating tool, the implant is transferred from the sterile sleeve to the site of use and is implanted therein without being directly touched.

Once the implant is driven to the desired depth in the bone tissue, the manipulating tool is removed, leaving the holding element fixedly resting on the implant. To remove the holding element an unscrewing force, e.g. through an unscrewing spanner, must be applied on the assembly composed of holding element and implant. This operation requires generally an amount of space which often is not available. Moreover, if the implant has been placed in particular in soft bone, the torque applied to remove a holding element may also lead to unscrew the entire assembly or to damage the implant surface/bone tissue interface. Transferring unwanted forces to the bone may cause necrosis of the interface bone tissue, and consequently mobilization of the implant may occur.

In order to avoid the negative effect of the unscrewing force, in these kind of implant systems, a counter torque tool is used, if possible, to prevent the torsional force transfer to the implant when the holding element is unscrewed and removed, depending on the implant structure and on the free space available at the implantation site.

U.S. Pat. No. 6,206,696 discloses a delivery system for implants of the above mentioned kind, comprising a dental implant and a holding element composed of a driving tool and a healing screw. The driving tool is designed to engage the healing screw in order to drive the implant during implantation. For this purpose it has an engagement feature which permits to simply hook or unhook from the healing screw.

The dental implant system disclosed by U.S. Pat. No. 6,206,696, does not offer the possibility to control the force applied during implantation and particularly while screwing in the implant, so that if a too strong force is applied, the thread of the healing screw may cant in the thread of the implant. After the healing period is completed a prosthesis has to be affixed.

SUMMARY OF THE INVENTION

The aim of the present invention is to provide an implant system, particularly a dental implant system, in which the implant is suitable to be positioned and retained in the bone tissue without directly contacting it with any contaminating agent and simultaneously minimizing the transmission of damaging forces to the implant, thus overcoming the above mentioned drawbacks, in particular avoiding the application of torsional and/or other damaging forces on the implant.

Within the scope of this aim, an object of the present invention is to provide a dental implant system which allows an easier implantation procedure, a restricted number of tools easy to handle, and which can be used even in case of narrow implantation sites.

Another object is to provide an implant system which allows a secure implantation procedure and reduces the injury risk by avoiding to loose the implant and/or to damage the implant surface/bone tissue interface while removing the holding element from the implant.

This aim, these objects and others which will become better apparent hereinafter, are achieved by an implant system according to claim 1. Further advantageous features are set forth in the dependent claims.

BRIEF DESCRIPTION OF THE DRAWINGS

Further characteristics and advantages of the present invention will become better apparent from the following description of a preferred but not exclusive embodiment of the implant system according to the invention, illustrated by way of non-limitative example in the accompanying drawings, wherein:

FIG. 1 is an exploded perspective view of the implant system according to the present invention;

FIG. 2 is a perspective view of the implant system of the present invention partially assembled.

FIG. 3 is a perspective view of the implant system of the present invention assembled with the separating tool;

FIG. 4 is a perspective view of the implant system of the present invention showing the separation of the holding elements and of the clamping element from the implant;

DESCRIPTION OF THE PREFERRED EMBODIMENTS

Figures 5, 6:
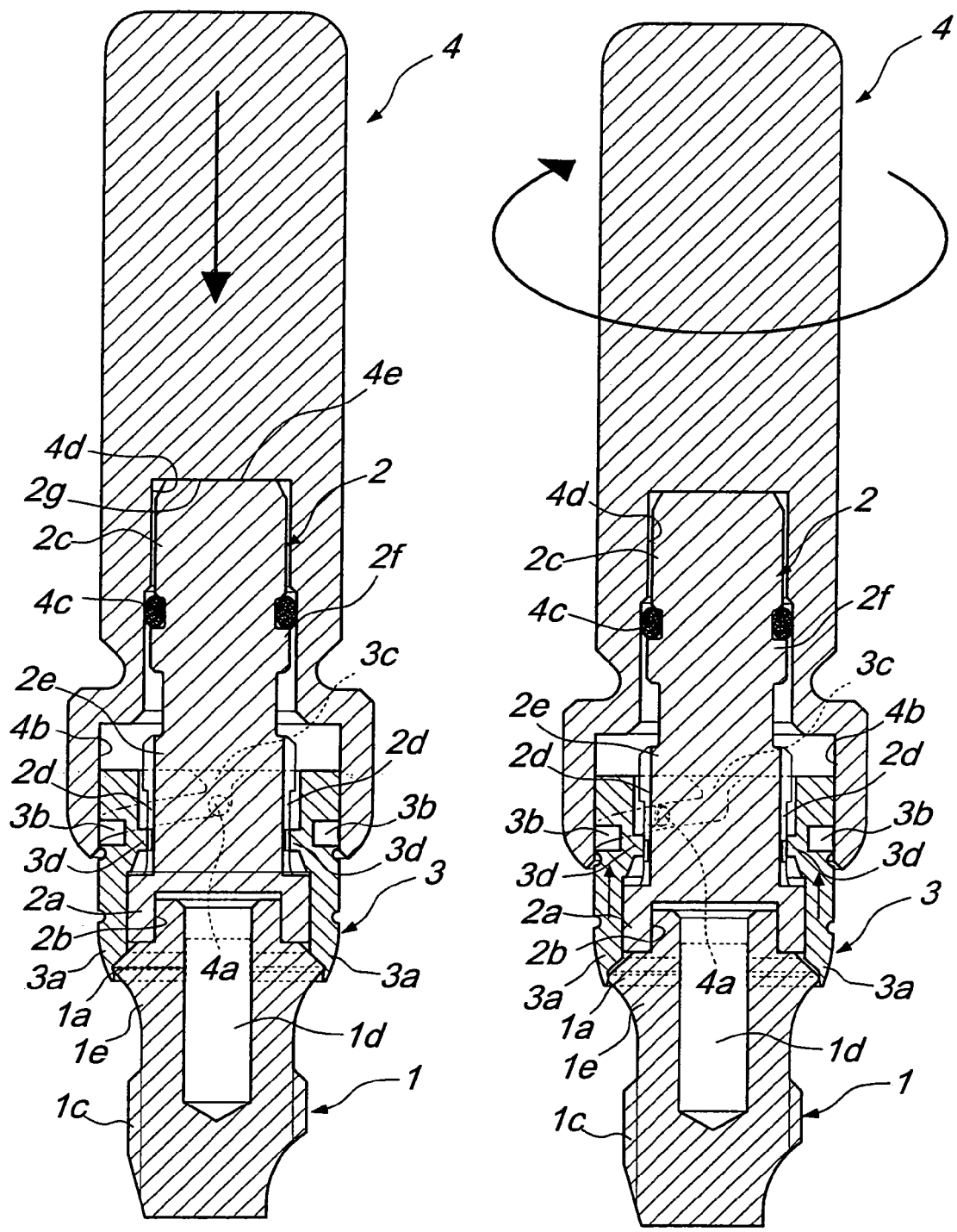
FIG. 5 is a cross-sectional view of the system of the present invention assembled and engaged with the separating tool.
FIG. 6 is a cross-sectional view of the system of the present invention during a first step of the disengagement of the clamping element from the implant achieved by rotating the separating tool.

The implant system of the present invention comprises a dental implant, e.g. a conventional threaded dental implant, and means suitable to hold, to position in the bone tissue, and to release in its final seat said implant, as described above.

With reference to FIG. 1, the implant system comprises a conventional dental implant 1, which may be for example a conventional substantially cylindrical or tapered threaded implant having a threaded portion 1c surrounding the external cylindrical or tapered body, this threaded portion 1c being suitable to be screwed in the bone tissue. The implant 1 further comprises a neck portion 1e, which will interact with the gingival tissue once the implant will be positioned in its final seat in the bone tissue. This neck portion 1e ends upwardly with a shoulder 1a. Such implant design is well known to the skilled in the art.

Upwardly to the shoulder 1a of the implant, extends a non-rotational contour 1b (e.g. a shaft or male with a spline profile) suitable to interact with a complementary non-rotational cavity 2b (see FIG. 5) (e.g. a cavity with a complementary spline profile) provided on a holding element 2.

Said holding element 2, as described in the background section of the present application, is commonly used during the implantation procedure to steadily hold the implant allowing to extract it from the sterile container or ampule (not shown) in which it is packaged and stored, and to positioning and screwing it into the bone tissue avoiding to touch the implant with the hands or to contact it with any contaminating agent. The holding element 2 has a substantially cylindrical body provided with a bottom end 2a which is adapted to connect the implant 1. Between said implant 1 and said holding element 2, non-rotational connection means are provided, said non-rotational connection means comprising the above mentioned non-rotational contour 1b and the complementary non-rotational cavity 2b provided on said holding element 2.

Generally, in the prior art, the end suitable to connect the implant 1 is threaded in order to connect the implant by means of the internal threaded bore 1d of the implant 1 and this leads to the above mentioned disadvantages related to the unscrew action.

In the present invention, the holding element 2 presents the non-rotational cavity 2b, which is complementary to said non-rotational contour 1b provided on the implant. The presence of a non-rotational joint between said holding element 2 and said implant 1 allows to use the holding element 2 to screw the implant 1 into the bone tissue during the implantation procedure. The holding element has a top end 2c, which has a non-rotational profile, in particular a common polygonal profile.

In order to retain said holding element 2 close to said implant 1 both during the transferring procedure consisting of extracting the implant 1 from the sterile packaging and positioning it in an adapted bore in the bone tissue, and during the screwing action of said implant 1 into the bone tissue until it reaches its final position, the implant system of the present invention comprises a further element which is referred to as clamping element 3. The clamping element 3 has a substantially hollow cylindrical shape provided with different internal diameters in order to interact with different portions of the external surface of said holding element 2.

In particular, the clamping element 3 comprises elastic means adapted to clamp the shoulder 1a of said implant 1, said elastic means consisting of the elastically deformable bottom end 3a of said clamping element 3.

Said clamping element 3 presents an inner surface 3e with a diameter, which is smaller with respect to the outer diameter of the bottom extremity 2a and larger with respect to the median portion 2e of the external surface of said holding element 2. Moreover, the clamping element 3 has two preferably diametrically opposed snugs 3d each one adapted to be inserted in a respective vertical groove 2d specially designed on the outer surface of the holding element 2. Said snugs 3d, when engaging said vertical grooves 2d, avoid the relative rotation of the clamping element 3 with respect to the holding element 2, while relative translational movements are allowed.

In order to separate said holding element 2 and said clamping element 3 from said implant 1, a dedicated tool is provided, which is referred to as separating tool 4.

The clamping element 3 and the separating tool 4 are further provided with release means adapted to release said implant 1 from said holding element 2 by minimizing transfer damaging forces to said implant 1, especially torsional forces. Said release means are adapted to lift said clamping element 3 upwardly in order to release the implant shoulder 1a from the clamping element 3 itself. Said release means comprises, at least an helical groove 3b provided on the external cylindrical surface of said clamping element 3, and at least one pin 4a adapted to be inserted in said helical groove 3b. Preferably, two diametrically opposed helical grooves 3b are provided, each one presenting an inlet slot 3c adapted to receive and lead the entrance into said groove 3b of an interference pin 4a provided on an separating tool 4.

Said separating tool 4 as shown in FIG. 1 has a substantially cylindrical external shape, adapted to be comfortably held, and has an inner cavity adapted to receive said holding element 2. More in detail, the inner cavity of the separating tool has a first internal portion 4b (see FIG. 5) which has a diameter adapted to fit with the external diameter of the clamping element 3, and it has also said two pins 4a which extend from the internal surface of this portion. Over this first internal portion, the separating tool 4 has a second portion 4c (see FIG. 5) and a third portion 4d (see FIG. 5) suitable to receive the upper-median portion 2f and the top end portion 2c of the holding element 2. As shown in FIGS. 5 to 9, when the separating tool 4 is assembled on the system formed by the implant 1, the holding element 2 and the clamping element 3, the top end 2c of the holding element 2 results to be engaged into the inner cavity of the separating tool 4. In particular, when the pin or pins 4a reach the position indicated in FIG. 5 the upper side 2g of the top end 2c of the holding element 2 becomes engaged with the bottom side of 4e the inner cavity of the separating tool 4. Clearly this engagement can occur slightly before or after the shown position of the pin or pins 4a.

Optionally an O-Ring retention element can be provided on the holding element 2 at an adapted region, such as, for example, at the second portion 4c of the separating tool 4, in order to create an additional retention (friction) force between the holding element 2 and the separating tool 4.

The implantation procedure of the system of the present invention comprises the following steps.

The top end 2c, which has a polygonal external profile, projects out of the ampule permitting in this way to attach to the assembly a manipulating tool (not shown) like, for instance, a dental handpiece. Due to this manipulating tool the implant can be transported to the implantation site and can be implanted without getting in contact with non-sterile parts.

The implant 1 and the holding element 2 are joined together by means of the clamping element 3 and these assembled elements are stored in a common sterile packaging, e.g. an ampule, and the top end 2c, which has a polygonal external profile, projects out of the ampule. In order to extract the assembled implant system from the packaging or the ampule, an adapted conventional manipulating tool (not shown) can be connected to the top end 2c of the holding element 2. By means of this manipulating tool, the implant 1 can be both extracted from the packaging and also screwed in the bone tissue without touching it with the hands, also avoiding that the implant come in contact with any contaminating agent.

Once the implant has been screwed in the bone tissue, the manipulating tool is removed and the assembled implant consisting of the implant 1, the holding element 2 and the clamping element 3, as shown in FIG. 2, remains steady screwed in its final seat in the bone tissue.

Next, the holding element 2 and the clamping element 3 have to be removed from the implant. For this purpose, the separating tool 4 (FIG. 2) is inserted over the holding element 2, as shown in FIG. 3, with the pins 4a that engage the slots 3c (FIG. 5) and the top end of the holding element 2 leans against the top end of the inner cavity of the separating tool 4, so avoiding relative translatory movements between the separating tool 4 and the holding element 2. When the separating tool 4 is rotated around its longitudinal axis, the pins 4a slide inside the grooves 3b. Due to the helical shape of the grooves 3b, when the pins 4a slide into the grooves 3b the clamping element 3 is lifted upwardly, and consequently the bottom end 3a thereof is disengaged from the implant shoulder 1a (as illustrated in FIGS. 6, 7 and 9), resulting in that the holding element 2 is no more retained to the implant 1 and therefore the holding element 2 can be simply pulled away from the implant 1 together with the separating tool 4.

Figures 7, 8:
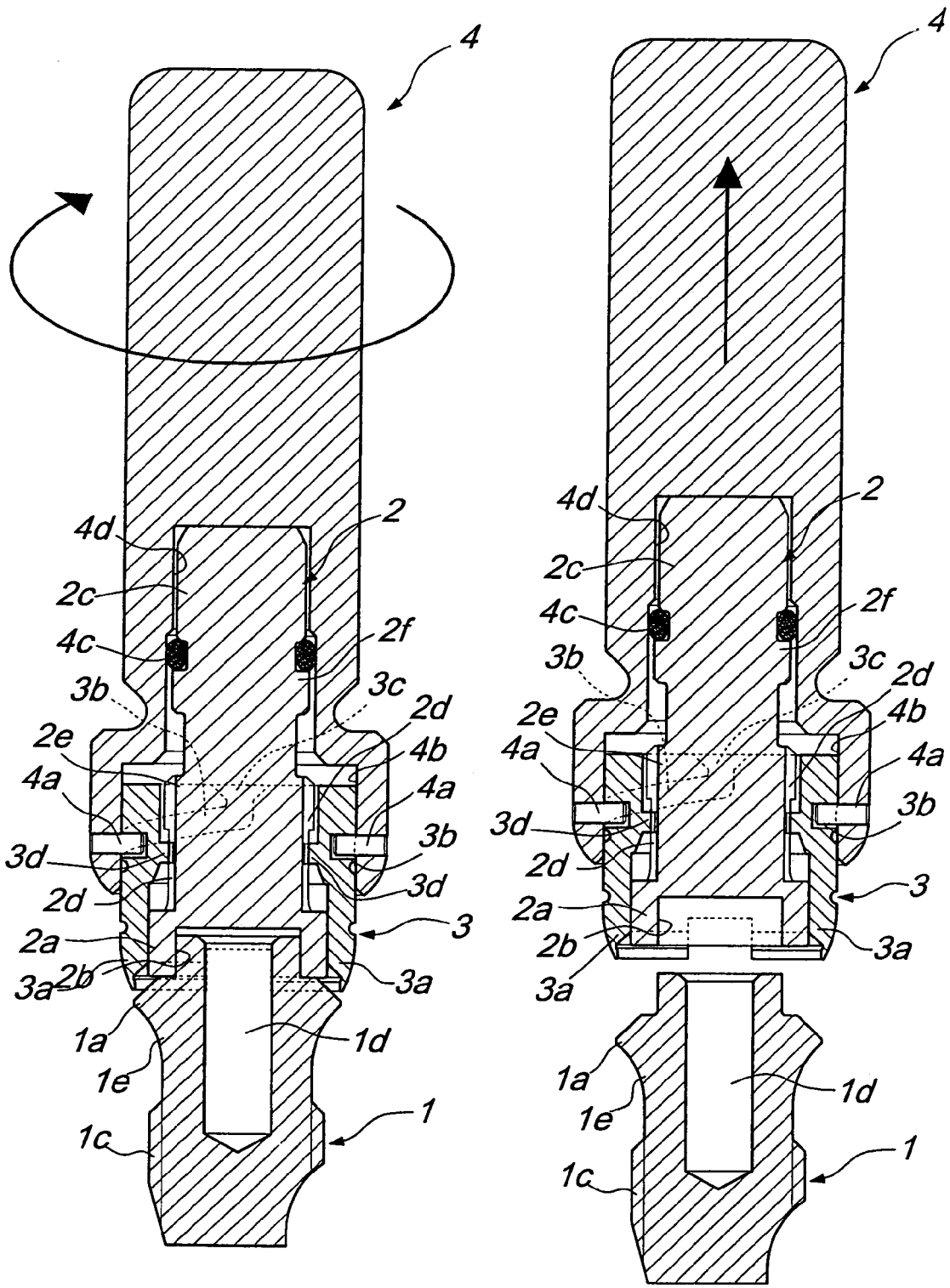
FIG. 7 is a cross-sectional view of the system of the present invention during a subsequent step of the disengagement of the clamping element from the implant achieved by rotating the separating tool.
FIG. 8 is a cross-sectional view of the system of the present invention during the last step of the disengagement of the holding element from the implant achieved by pulling away the separating tool.
Figure 9:
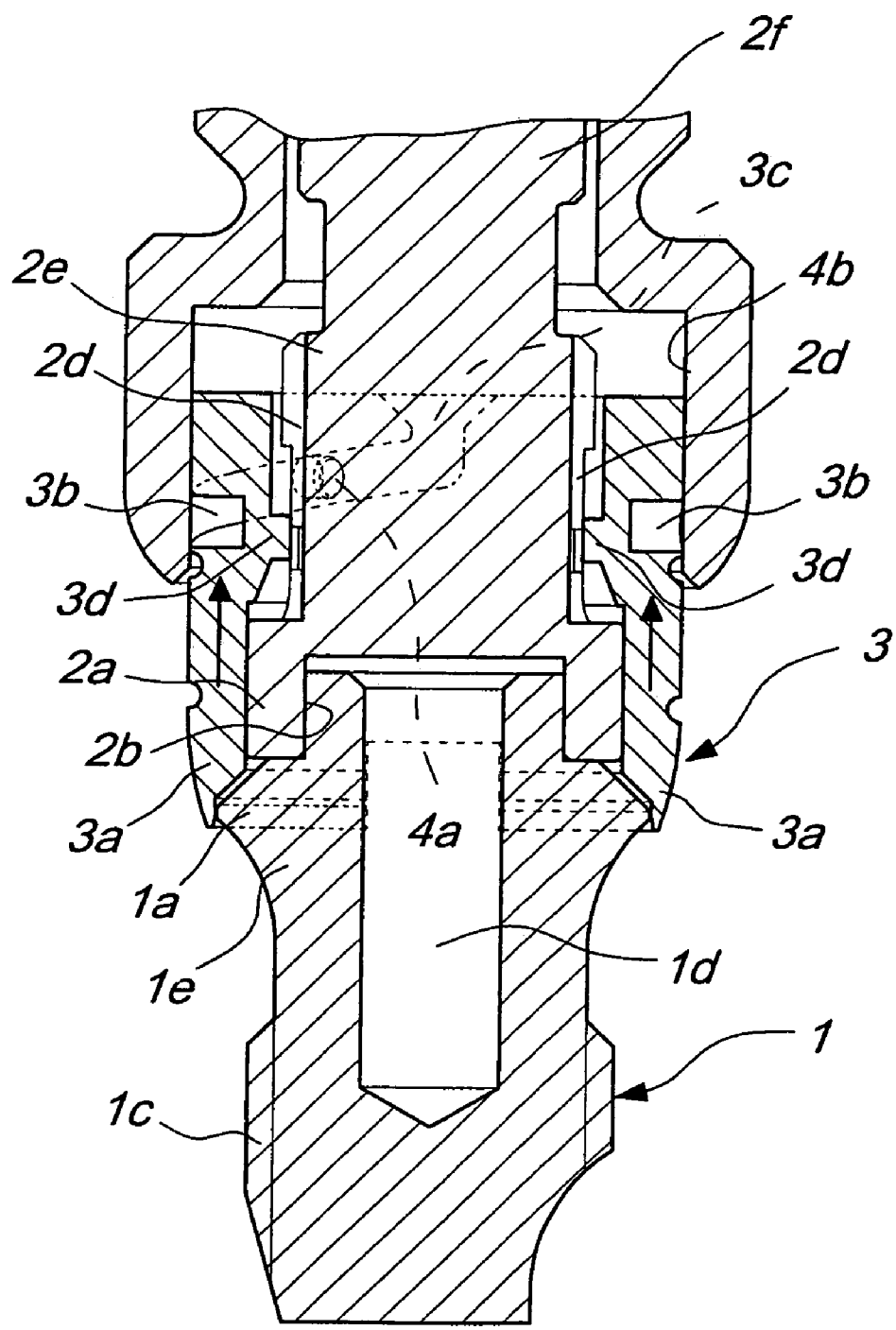
FIG. 9 is an enlarged detail of FIG. 6 exemplifying the separation of the dental implant.

As apparent from FIGS. 5 through 7 the clamping element 3 is moved prior to the separation of the implant 1 axially in an upward direction as indicated by the arrows of FIG. 6 or 9 while the implant 1, the holding element 2 and the tool 4 remain axially engaged. Further, as apparent from FIG. 8, following the upward movement of the clamping element 3, the bottom end 3a gets separated from the shoulder 1a, such that elements 2 and 3 are released. As the holding element 4, the separating tool 4 and the clamping element 3 are secured by aspiration the present invention avoids that said elements 2 and 3 are swallowed by the patient during the separation of the implant 1.

It has thus been shown that the present invention fulfills the proposed aim providing an implant system which allows to position and to screw an implant, particularly a dental implant, in the bone tissue and finally to release it in its final seat without directly taking said implant with the hands or contacting it with any contaminating agent and simultaneously minimizing the transmission of damaging forces, such as compressive, tensile and torsional forces, from the tools to the implant and consequently damaging forces to the bone tissue.

In order to achieve this aim, the joint between an holding element and the implant has been specially designed and a clamping element has been provided in order to simply clamp and release said implant from said holding element.

Further it has been shown that the present invention as described fulfills the proposed object of providing an implant system which comprises tools easy to handle and which can be easily positioned even in case of narrow implantation sites because it provides tools which do not require a large free area around the implant. In fact, they act in a narrow region around the implant and substantially coaxially thereto.

Another object achieved by the present invention is that the joint realized between the separating tool 4 and the assembled system comprising the holding element 2 and the clamping element 3, is safe and steady so that when the separating tool 2 is lifted by the user in order to separate the clamping element 3 and the holding element 2 from the implant 1, the risk of losing the holding element 2 and/or the clamping element 3 in reduced, and finally the safety of the patient is improved.

Clearly, several modifications will be apparent to and can be readily made by the skilled in the art without departing from the scope of the present invention. Therefore, the scope of the claims shall not be limited by the illustrations or the preferred embodiments given in the description in the form of examples, but rather the claims shall encompass all of the features of patentable novelty that reside in the present invention, including all the features that would be treaded as equivalents by the skilled in the art.

The disclosures in European Patent Application No. 04018636.3 from which this application claims priority are incorporated herein by reference.

What is claimed is:

1. An implant system comprising a dental implant and a holding element, wherein said implant system further comprises non-rotational joint means adapted to avoid relative rotation of said holding element with respect to said implant, and a clamping element adapted to steadily retain said holding element close to said implant, including a separating tool, the system further comprising release means provided on said clamping element and interacting with release means provided on said separating tool, said release means on said clamping element comprising at least one helical groove provided on the external surface of said clamping element and at least one pin provided on said separating tool, said pin being insertable in said helical groove so that, when rotating said separating tool around its longitudinal axis, said pin slides along said helical groove and said clamping element is lifted upwardly and disengaged from said implant shoulder by means of an elastic deformation of said bottom end, so that by acting on said separating tool said implant can be released from said holding element minimizing the transfer of damaging forces such as torsional, tensile or compressive forces to said implant.

2. The implant system according to claim 1, wherein the release means provided on said clamping element and the release means provided on the separating tool are adapted to interact so as to cause movement of the clamping element in an axial direction of the implant and away from the implant.

3. The implant system according to claim 2, wherein the holding element is adapted to rotationally hold the implant and in that the release means provided on said clamping element and the release means provided on the separating tool are further adapted to interact so as to cause movement of the clamping element in an axial direction of the holding element.

4. The implant system according to claim 3, wherein it is further adapted to keep the implant and the holding element axially engaged during a substantial part of the axial movement of the clamping element.

5. The implant system according to claim 1, wherein the clamping element includes elastic means adapted to clamp a portion of the implant.

6. The implant system according to claim 1, wherein said clamping element has a hollow substantially cylindrical shape and has an elastically deformable bottom end defining the elastic means and suitable to elastically clamp a shoulder provided on said implant, said clamping element having different portions with different internal diameters each adapted to respectively interact with an external portion of said holding element in order to retain said holding element close to said implant when the clamping element is clamped to said implant shoulder and allowing said clamping element to translate upwardly with respect to said holding element when said clamping element is released from said implant shoulder.

7. The implant system according to claim 1, wherein said clamping element further comprises at least one snug protruding from its internal surface and which is inserted in a respective vertical groove provided on the outer surface of said holding element in order to avoid relative rotational movement of said clamping element with respect to said holding element.

8. The implant system according to claim 7, wherein said separating tool has a substantially cylindrical external shape adapted to be comfortably held and has an inner cavity adapted to receive said holding element.

9. An implant system comprising a dental implant and a holding element, wherein said implant system further comprises non-rotational joint means adapted to avoid relative rotation of said holding element with respect to said implant, and a clamping element adapted to steadily retain said holding element close to said implant, including a separating tool, the system further comprising release means provided on said clamping element and suitable to interact with release means provided on said separating tool, said release means on said clamping element comprising at least one helical groove provided on the external surface of said clamping element and at least one pin provided on said separating tool, said pin being insertable in said helical groove so that, when rotating said separating tool around its longitudinal axis, said pin slides along said helical groove and said clamping element is lifted upwardly and disengaged from said implant shoulder by means of an elastic deformation of said bottom end, so that by acting on said separating tool said implant can be released from said holding element minimizing the transfer of damaging forces such as torsional, tensile or compressive forces to said implant, wherein the release means provided on said clamping element and the release means provided on the separating tool are adapted to interact so as to cause movement of the clamping element in an axial direction of the implant and away from the implant, the holding element rotationally holding the implant, and the release means provided on said clamping element and the release means provided on the separating tool further interacting so as to cause movement of the clamping element in an axial direction of the holding element.

10. The implant system according to claim 9, wherein it is further adapted to keep the implant and the holding element axially engaged during a substantial part of the axial movement of the clamping element.

11. The implant system according to claim 9, wherein the clamping element includes elastic means adapted to clamp a portion of the implant.

12. The implant system according to claim 9, wherein said clamping element has a hollow substantially cylindrical shape and has an elastically deformable bottom end defining the elastic means and suitable to elastically clamp a shoulder provided on said implant, said clamping element having different portions with different internal diameters each adapted to respectively interact with an external portion of said holding element in order to retain element close to said implant when the clamping element is clamped to said implant shoulder and allowing said clamping element to translate upwardly with respect to said holding element when said clamping element is released from said implant shoulder.

13. The implant system according to claim 9, wherein said clamping element further comprises at least one snug protruding from its internal surface and which is inserted in a respective vertical groove provided on the outer surface of said holding element in order to avoid relative rotational movement of said clamping element with respect to said holding element.

14. The implant system according to claim 13, wherein said separating tool has a substantially cylindrical external shape adapted to be comfortably held and has an inner cavity adapted to receive said holding element.

15. An implant system comprising a dental implant and a holding element, wherein said implant system further comprises non-rotational joint means adapted to avoid relative rotation of said holding element with respect to said implant, and a clamping element adapted to steadily retain said holding element close to said implant, including a separating tool, the system further comprising release means provided on said clamping element and suitable to interact with release means provided on said separating tool, so that by acting on said separating tool said implant can be released from said holding element minimizing the transfer of damaging forces such as torsional, torsional, tensile or compressive forces to said implant, wherein said release means on said clamping element comprise at least one helical groove provided on the external surface of said clamping element and at least one pin provided on said separating tool, said pin being insertable in said helical groove so that, when rotating said separating tool around its longitudinal axis, said pin slides along said helical groove and said clamping element is lifted upwardly and disengaged from said implant shoulder by means of an elastic deformation of said bottom end.

16. The implant system according to claim 15, wherein the clamping element includes elastic means adapted to clamp a portion of the implant.

17. The implant system according to claim 15, wherein said clamping element has an hollow substantially cylindrical shape and has an elastically deformable bottom end defining the elastic means and suitable to elastically clamp a shoulder provided on said implant, said clamping element having different portions with different internal diameters each adapted to respectively interact with an external portion of said holding element in order to retain said holding element close to said implant when the clamping element is clamped to said implant shoulder and allowing said clamping element to translate upwardly with respect to said holding element when said clamping element is released from said implant shoulder.

18. The implant system according to claim 15, wherein said clamping element further comprises at least one snug protruding from its internal surface and which is inserted in a respective vertical groove provided on the outer surface of said holding element in order to avoid relative rotational movement of said clamping element with respect to said holding element.

19. The implant system according to claim 18, wherein said separating tool has a substantially cylindrical external shape adapted to be comfortably held and has an inner cavity adapted to receive said holding element.

* * * * *